(12) United States Patent
Kohno et al.

(10) Patent No.: US 6,175,045 B1
(45) Date of Patent: Jan. 16, 2001

(54) PROCESS FOR THE PREPARATION OF PENTAFLUOROETHANE

(75) Inventors: Satoru Kohno; Takashi Shibanuma, both of Osaka (JP)

(73) Assignee: Daikin Industries Ltd., Osaka (JP)

( * ) Notice: Under 35 U.S.C. 154(b), the term of this patent shall be extended for 0 days.

(21) Appl. No.: 09/424,317

(22) PCT Filed: May 18, 1998

(86) PCT No.: PCT/JP98/02170

§ 371 Date: Nov. 22, 1999

§ 102(e) Date: Nov. 22, 1999

(87) PCT Pub. No.: WO98/52889

PCT Pub. Date: Nov. 26, 1998

(30) Foreign Application Priority Data

May 22, 1997 (JP) .................................................. 9-132059

(51) Int. Cl.[7] .............................. C07C 17/38; B01D 3/34
(52) U.S. Cl. ............................. 570/178; 570/180; 203/57; 203/98
(58) Field of Search ................................. 570/178, 180; 203/57, 98, 62, 70, 63, 66, 67, 68

(56) References Cited

U.S. PATENT DOCUMENTS

| 3,689,374 | 9/1972 | Hanson . |
|---|---|---|
| 5,087,329 | 2/1992 | Felix . |
| 5,919,340 | 7/1999 | Kohno et al. .................. 570/178 |

FOREIGN PATENT DOCUMENTS

| 07133240 | 5/1995 | (JP) . |
| 08003082 | 1/1996 | (JP) . |
| WO9606063 | 2/1996 | (WO) . |

*Primary Examiner*—Alan Siegel
(74) *Attorney, Agent, or Firm*—Birch, Stewart, Kolasch & Birch, LLP

(57) ABSTRACT

There is provided a process of effectively separating pentafluoroethane (HFC-125) from a mixture of HFC-125 and chloropentafluoroethane (CFC-115).

When the mixture of HFC-125 and CFC-115 is subjected to an extractive distillation to obtain a concentrated HFC-125, ethyleneglycol-based compounds (3) having a general formula:

$$R^1O(CH_2CH_2O)_nR^2$$

wherein $R^1$ and $R^2$ may be the same or different and are each independently selected from the group consisting of hydrogen and an alkyl group having 1 to 4 carbon atoms, and n is an integer with a value from 1 to 3 is used as an extractant, whereby CFC-115 is obtained as a distillate product (4) and a mixture of HFC-125 and the extractant as a bottom product (5) is obtained. Then, the extractant is separated from HFC-125 by distilling the mixture and re-used in the extractive distillation.

7 Claims, 1 Drawing Sheet

PROCESS FOR THE PREPARATION OF PENTAFLUOROETHANE

This application is a 371 of PCT/JP98/02170 filed May 18, 1998.

TECHNICAL FIELD

The present invention relates to a process of producing pentafluoroethane characterized in that pentafluoroethane is separated from a mixture comprising at least pentafluoroethane (hereinafter, also referred to as "HFC-125") and chloropentafluoroethane (hereinafter, also referred to as "CFC-115"), for example a reaction product from a production process for pentafluoroethane through fluorination of tetrachloroethylene, through extractive distillation process using a particular compound as an extracting agent (solvent).

BACKGROUND ART

HFC-125 is a useful compound as an alternative chlorofluorocarbon (or flon) compound free of chlorine and is used as a cooling medium, a blowing agent, an injecting propellant and so on. HFC-125 is conventionally produced through a fluorination process of tetrachloroethylene. In such a production process, dichlorotetrafluoroethane, dichlorotrifluoroethane, hexafluoroethane, CFC-115 and so on are produced as by-products.

Among those by-products, CFC-115 has a boiling point of −38.7° C. which is close to a boiling point of HFC-125 of −48.5° C. Further, a value of the relative volatility between these two compounds is close to 1. Particularly, when a mixture contains HC-125 at a concentration of not less than 95 mole % (that is, the concentration of CFC-115 is not more than 5 mole %), the relative volatility value is about 1.04. Accordingly, when the above mixture is distilled to separate HFC-125 at a high concentration through a conventional distillation treatment, a distillation apparatus having much plate numbers is required, which generally means that the separation using distillation is extremely difficult.

In the present specification, when a solution essentially comprising of at least a remarked component A and a remarked component B (a boiling point of component A<a boiling point of component B) is in a vapor-liquid equilibrium state with the vapor thereof, the term "relative volatility (α)" is defined as follows:

$$\alpha = (Y_A/X_A)/(Y_B/X_B)$$

wherein, $X_A$ is a molar fraction of the lower boiling component A in the liquid phase, $X_B$ is a molar fraction of the higher boiling component B in the liquid phase, $Y_A$ is a molar fraction of the lower boiling component A in the vapor phase which is in equilibrium with its liquid phase, and $Y_B$ is a molar fraction of the higher boiling component B in such vapor phase.

DISCLOSURE OF INVENTION

In order to recover one component from a mixture of a system having a relative volatility value of around 1, an extractive distillation process is adopted. As an example of the extractive distillation process to separate a mixture comprising HFC-125 and CFC-115, U.S. Pat. No. 5,087,329 discloses an extractive distillation process using fluorocarbon compound having 1 to 4 carbon atoms as an extractant.

In the process disclosed in U.S. Pat. No. 5,087,329, a value of the relative volatility between HFC-125 and CFC-115 is almost 1.2 based on a calculation using figures shown in Example 1 thereof. Thus, when the concentration of HFC-125 is intended to increase to a ratio of HFC-125/CFC-115=99.7 mole %/0.3 mole % from a mixture having a ratio of HFC-125/CFC-115=7 mole %/93 mole %, a theoretical plate number amounting almost to 40 plates is required in that system. This theoretical plate number was obtained according to after-mentioned calculation method.

As a result of extensive studies on a process to separate HFC-125 from a mixture comprising HFC-125 and CFC-115 through an extractive distillation process with high efficiency, the present inventors found the matters as follows:

When a mixture comprising at least HFC-125 and CFC-115 is subjected to an extractive distillation process, HFC-125 may be separated from the above mixture, for example, using a distillation column having a very small theoretical plate number using, as an extractant (or a solvent), at least one compound (thus, a single compound or a mixture of two or more compounds) selected from ethyleneglycol-based compounds having a general formula:

$$R^1O(CH_2CH_2O)_nR^2$$

wherein $R^1$ and $R^2$ may be the same or different and are each independently selected from the group consisting of hydrogen and an alkyl group having 1 to 4 carbon atoms, and n is an integer with a value from 1 to 3.

Accordingly, the present invention provides a process of separating HFC-125 from a mixture comprising at least HFC-125 and CFC-115 through an extractive distillation process, characterized in that at least one ethyleneglycol-based compounds aforementioned is used as an extractant to obtain HFC-125 in which a concentration of CFC-115 is relatively reduced, and preferably highly concentrated HFC-125 which is free of CFC-115.

That is, the present invention provides a process of producing pentafluoroethane in which a mixture comprising at least pentafluoroethane and chloropentafluoroethane as a main component thereof is subjected to an extractive distillation to obtain another mixture which contains pentafluoroethane as a main component thereof and does not substantially contain chloropentafluoroethane, characterized in that at least one ethyleneglycol-based compounds is used as an extractant to obtain a mixture comprising pentafluoroethane and the extractant as a bottom product of the extractive distillation step.

Figure 1:
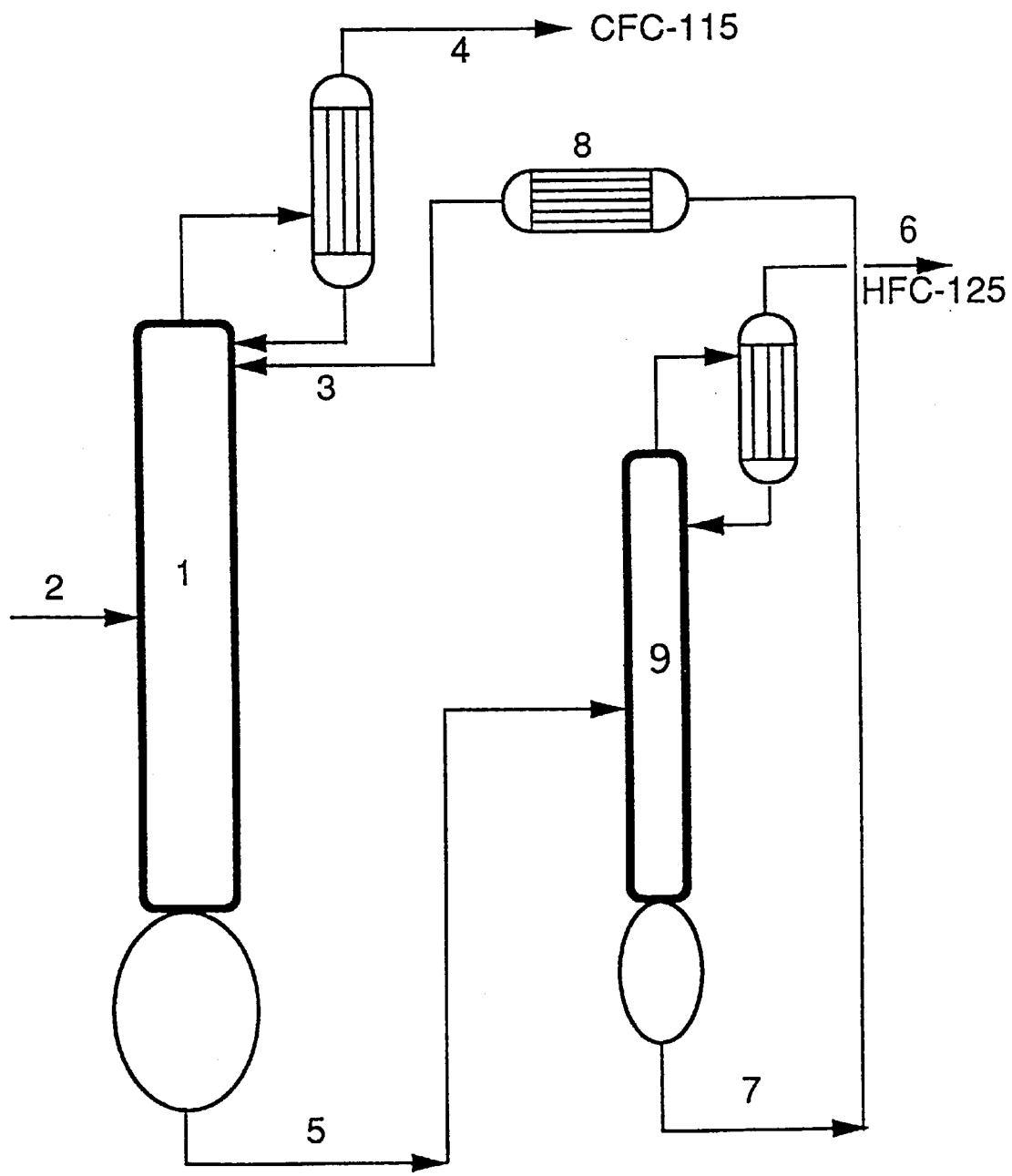
FIG. 1 is a flow sheet schematically showing one concrete embodiment for performing the process of the present invention.

In the FIG. 1, the numeral 1 represents an extractive distillation unit, the numeral 2 represents a mixture comprising HFC-125 and CFC-115, the numeral 3 represents an extractant, the numeral 4 represents a distillate, the numeral 5 represents a bottom product, the numeral 6 represents another distillate, the numeral 7 represents another bottom product, and the numeral 8 represents a heat-exchanger, and the numeral 9 represents a separative distillation unit of HFC-125.

BEST MODE FOR CARRYING OUT THE INVENTION

In the present specification, the term "main component" means that the content of the other components is relatively smaller than the content of the main component in the mixture. Concretely, it is sufficient that an amount of the main component is not less than 50% (for example, not less than 50% on a molar or weight basis), more concretely not less than 60%, for example not less than 80%. Further, the "main component" may consist of one component solely, or consist of two or more components together. In the present case, for example, the main component may consist of two components such as pentafluoroethane and the extractant together.

Additionally, in the present specification, the phrase "pentafluoroethane substantially free of chloropentafluoroethane" means that the finally obtainable product is a mixture including pentafluoroethane as its main component, wherein for example, such a mixture may have a concentration of pentafluoroethane not less than 90 weight %, preferably not less than 99.9 weight %, and more preferably not less than 99.9 weight %.

According to the present process, a mixture may be obtained as a bottom product, which contains pentafluoroethane and the extractant as the main component thereof, preferably such a mixture contains chloropentafluoroethane at a concentration not more than 0.1 weight %, and more preferably not more than 0.01 weight %. In this case, the composition of the distillate product from the extractive distillation is not limited provided that a ratio of chloropentafluoroethane to pentafluoroethane in the bottom product is reduced by somewhat an extent from an original ratio thereof, preferably the ratio is reduced to not more than 1/10 of the original ratio, and more preferably reduced to not more than 1/100 of the original ratio. In addition, the distillate product may contain, as a main component thereof, chloropentafluoroethane or pentafluoroethane or a mixture of chloropentafluoroethane and pentafluoroethane.

In one embodiment of the present invention, the mixture comprising at least pentafluoroethane and chloropentafluoroethane as its main component substantially consists of two components which are HFC-125 and CFC-115.

In another embodiment of the present invention, pentafluoroethane may be separated from the extractant by subjecting the bottom product from the extractive distillation, for example a bottom product containing the extractant and pentafluoroethane as its main component, to a distillation treatment in the other step. Thereafter, the extractant may be recovered and recycled to the extractive distillation treatment step.

In the present invention, the term "extractive distillation" means a distillation procedure which is used in the present technical field, in particular in the field of the chemical engineering, characterised in that distillative separation of two components, which are difficult to separate each other through a general distillation procedure, are facilitated by deviating the relative volatility value of the original two-component system from a value one at a considerable extent.

The ethyleneglycol-based compounds which may be used in the present invention are exemplified, but they are not limited to such examples, as follows:

(1) Ethyleneglycol monoalkylether or polyethyleneglycol monoalkylether represented by a general formula:

$$RO(CH_2CH_2O)_nR$$

wherein R represents $CH_3$, $C_2H_5$, $C_3H_7$ (particularly n- or iso-$C_3H_7$) or $C_4H_9$ (particularly n- or tert-$C_4H_9$) and n is an integer with a value from 1 to 3;

(2) Ethyleneglycol dialkylether or polyethyleneglycol dialkylether represented by a general formula:

$$RO(CH_2CH_2O)_nR$$

wherein R represents $CH_3$, $C_2H_5$, $C_3H_7$ (particularly n- or iso-$C_3H_7$) or $C_4H_9$ (particularly n- or tert-$C_4H_9$) and n is an integer with a value from 1 to 3; and (3) Ethyleneglycol or polyethyleneglycol represented by a general formula:

$$HO(CH_2CH_2O)_nH$$

wherein n is an integer with a value from 1 to 3.

More concretely, the following compounds may be exemplified:

(1) $CH_3O(CH_2CH_2O)H$ (ethyleneglycol monomethylether), $CH_3O(CH_2CH_2O)_2H$ (diethyleneglycol monomethylether), $CH_3O(CH_2CH_2O)_3H$ (triethyleneglycol monomethylether), $C_2H_5O(CH_2CH_2O)H$ (ethyleneglycol monoethylether), $C_2H_5O(CH_2CH_2O)_2H$ (diethyleneglycol monoethylether), $C_2H_5O(CH_2CH_2O)_3H$ (triethyleneglycol monoethylether), $C_3H_7O(CH_2CH_2O)H$ (ethyleneglycol monopropylether), $C_3H_7O(CH_2CH_2O)_2H$ (diethyleneglycol monopropylether), $C_3H_7O(CH_2CH_2O)_3H$ (triethyleneglycol monopropylether), $C_4H_9O(CH_2CH_2O)H$ (ethyleneglycol monobutylether), $C_4H_9O(CH_2CH_2O)_2H$ (diethyleneglycol monobutylether), $C_4H_9O(CH_2CH_2O)_3H$ (triethyleneglycol monobutylether), (2) $CH_3O(CH_2CH_2O)CH_3$ (ethyleneglycol dimethylether), $CH_3O(CH_2CH_2O)_2CH_3$ (diethyleneglycol dimethylether), $CH_3O(CH_2CH_2O)_3CH_3$ (triethyleneglycol dimethylether), $C_2H_5O(CH_2CH_2O)C_2H_5$ (ethyleneglycol diethylether), $C_2H_5O(CH_2CH_2O)_2C_2H_5$ (diethyleneglycol diethylether), $C_2H_5O(CH_2CH_2O)_3C_2H_5$ (triethyleneglycol diethylether), $C_3H_7O(CH_2CH_2O)C_3H_7$ (ethyleneglycol dipropylether), $C_3H_7O(CH_2CH_2O)_2C_3H_7$ (diethyleneglycol dipropylether), $C_3H_7O(CH_2CH_2O)_3C_3H_7$ (triethyleneglycol dipropylether), $C_4H_9O(CH_2CH_2O)C_4H_9$ (ethyleneglycol dibutylether), $C_4H_9O(CH_2CH_2O)_2C_4H_9$ (diethyleneglycol dibutylether), $C_4H_9O(CH_{2CH2}O)_3C_4H_9$ (triethyleneglycol dibutylether), (3) $HO(CH_2CH_2O)H$ (ethyleneglycol), $HO(CH_2CH_2O)_2H$ (diethyleneglycol), $HO(CH_2CH_2O)_3H$ (triethyleneglycol).

The present inventors have studied the extractants as described above which are used in the process of separating HFC-125 from the mixture comprising HFC-125 and CFC-115 by extractive distillation, and obtained measurements of the relative volatilities between HFC-125 and CFC-115 which are shown in Table 1 below:

TABLE 1

| Extractant | Extractant Ratio*) | Relative Volatility ($\alpha$) |
|---|---|---|
| (a) $CH_3O(CH_2CH_2O)H$ (ethyleneglycol monomethylether) | 64 | 0.26 |
| (b) $CH_3O(CH_2CH_2O)_2H$ (diethyleneglycol monomethylether) | 59 | 0.25 |
| (c) $C_2H_5O(CH_2CH_2O)_2H$ (diethyleneglycol monoethylether) | 62 | 0.26 |
| (d) $C_4H_9O(CH_2CH_2O)_2H$ (diethyleneglycol mono-butylether) | 67 | 0.38 |
| (e) $C_2H_5O(CH_2CH_2O)_3H$ (triethyleneglycol monoethylether) | 60 | 0.26 |
| (f) $CH_3O(CH_2CH_2O)CH_3$ (ethyleneglycol dimethylether) | 45 | 0.4 |

TABLE 1-continued

| Extractant | Extractant Ratio*) | Relative Volatility (α) |
|---|---|---|
| (g) CH$_3$O(CH$_2$CH$_2$O)$_2$CH$_3$ (diethyleneglycol dimethylether) | 32 | 0.43 |
| (h) C$_4$H$_9$O(CH$_2$CH$_2$O)$_2$C$_4$H$_9$ (diethyleneglycol di-n-butylether) | 42 | 0.43 |
| (i) CH$_3$O(CH$_2$CH$_2$O)$_3$CH$_3$ (triethyleneglycol dimethylether) | 32 | 0.4 |
| (j) HO(CH$_2$CH$_2$O)$_2$H (diethyleneglycol) | 69 | 0.40 |
| (k) HO(CH$_2$CH$_2$O)$_3$H (triethyleneglycol) | 60 | 0.41 |

*) Extractant Ratio = (weight of extractant)/(sum of the weights of HFC-125 and CFC-115)
HFC-125/CFC-115 = 99.9/0.1 (wt/wt)

When the measurements of Table 1 were obtained, the following manner was employed: After a sealed vessel was evacuated to an almost vacuum pressure, predetermined amounts of HFC-125, CFC-115 and the extractant, each of them being in liquid phase, were charged into the vessel and were allowed to reach a vapor-liquid equilibrium state at a temperature of 20° C. Then, the liquid phase and the vapor phase were analyzed using gas chromatography to obtain compositions of the both phases as molar fractions. The relative volatility α was calculated using the above equation:

$$\alpha = (Y_A/X_A)/(Y_B/X_B).$$

As clearly seen from Table 1, it has been confirmed that the relative volatility value alpha (α) is considerably smaller than one in all the weight ratios as to each extractant, so that the addition of such extractant into the mixture of HFC-125 and CFC-115 at various extractant ratios leads to effective separation of CFC-115 as a volatile component, namely use of the above mentioned ethyleneglycol-based compounds as the extractant is suitable when separation of the HFC-125/CFC-115 mixture is carried out using the extractive distillation. For example, when HFC-125 is intended to be separated from the mixture comprising at least HFC-125 and CFC-115, it is expected that the distillation would be carried out using a distillation apparatus which has much smaller number of theoretical plates than a conventional apparatus.

Generally, when a mixture comprising HFC-125 and CFC-115 is subjected to a distillation operation, HFC-125 is concentrated into an enriching section at a top side of a column (that is, HFC-125 comes to a volatile component) since its boiling point is lower than that of CFC-115. However, on the contrary, when the relative volatility value is smaller than 1, CFC-115 is concentrated into the top side of the column.

Then, the separation process of the present invention will be hereinafter compared with Example described in U.S. Pat. No. 5,087,329 as to the number of theoretical plates of an extractive distillation column which is required for example when concentrated HFC-125 (e.g. a mixture of HFC-125 (99.9 mol %)/CFC-115 (0.1 mol %)) is to be obtained from a mixture of HFC-125 (90 mol %)/CFC-115 (10 mol %)

The process described in the above U.S. patent requires about 26 theoretical plates in order to produce a top distillate product of concentrated HFC-125 (e.g. concentrated to a mixture of HFC-125 (99.9 mol %)/CFC-115 (0.1 mol %)). In this case, calculation was carried out assuming the relative volatility to be a value of 1.2.

To the contrary, according to a process like the present invention which uses the extractant making the relative volatility value smaller than one, CFC-115 is concentrated into the top side of the column as a low boiling component. When the column has about six theoretical plates, a mixture of the extractant and HFC-125 which is concentrated to a ratio of HFC-125 (99.9 mol %)/CFC-115 (0.1 mol %) is produced as a bottom product, while a mixture in which a concentration of CFC-115 is increased from its original concentration to a ratio of HFC-125 (80 mol %)/CFC-115 (20 mol %) is obtained as a distillate product. In this case, calculation was carried out assuming the relative volatility to be 0.4.

The required number (N) of the theoretical plates referred to in the above was calculated according to the following equation:

$$\alpha^N = (Y_W/X_W)/(Y_D/X_D)$$

wherein α is a relative volatility, $X_D$ is a molar fraction of HFC-125 in a top distillate product, $X_W$ is a molar fraction of HFC-125 in a bottom product, $Y_D$ is a molar fraction of CFC-115 in a top distillate product and $Y_W$ is a molar fraction of CFC-115 in a bottom product.

When the extractant is used which makes the relative volatility value smaller than one, HFC-125 should be separated from the extractant so as to finally obtain HFC-125 alone since the bottom product from the extractive distillation step contains the extractant as described above. This separation is easily carried out with a conventional distillation operation using a plate column or a packed column since a boiling point difference is large between HFC-125 and the extractant. Thus, HFC-125 may be effectively separated out of the mixture comprising at least HFC-125 and CFC-115 by using combination of the extractive distillation operation with the distillation operation thereafter which separates the extractant.

If the mixture to be separated contains a third component in addition to HFC-125 and CFC-115, only difference resides in that the third component behaves together with HFC-125 and/or CFC-115 depending on a boiling point of the third component. Thus, even if the third component is contained in the mixture, HFC-125 is separated from CFC-115 by carrying out the extractive distillation using the extractant according to the present invention.

Further, with respect to the re-use of the extractant in the extractive distillation step, when the extractant disclosed in U.S. Pat. No. 5,087,329 is used, CFC-115 is concentrated into the bottom product and the extractant is also recovered from the distillation bottom. This means that the extractant contains a large amount of CFC-115, which necessitates separating CFC-115 from the extractant completely for the re-use of the extractant. If only a small amount of CFC-115 remains in the extractant, CFC-115 may be ultimately added to the extractive distillation step, whereby extraction efficiency may deteriorate and the required number of the theoretical plate may increase. In fact, it is estimated that the required number of the theoretical plate of a distillation apparatus would be about 10 to 20 in order to separate CFC-115 while the extraction efficiency does not deteriorate.

On the other hand, in the process according to the present invention in which the extractant making the relative volatility smaller than one is used, for example, the bottom product from the extractive distillation step is free of CFC-115 so that it is sufficient to separate only HFC-125 from the extractant. Therefore, even though HFC-125 remains in the extractant at a concentration of a few percentages and such extractant is re-used in the extractive distillation step, almost no effect is observed on the extraction efficiency. Thus, the number of theoretical plate of the distillation apparatus required for the recovery of the extractant is only about 2 to 5.

The extractive distillation process using the compound as the extractant according to the present invention can be carried out any distillation apparatus which is conventionally used such as a plate column, a packed column and so on. There are no specific limitations on various conditions of the distillation apparatus (such as an operation temperature, an operation pressure, a reflux ratio, a total plate number of the distillation apparatus, plate levels of mixture feed and extractant feed and so on), and proper conditions are selected depending on aimed separation. Since HFC-125 and CFC-115 have considerably low boiling points, it is generally preferable to carry out the extractive distillation under a pressurized condition. The operation pressure may be for example in the range between 0 and 50 $Kg/cm^2$-G (gauge pressure), and preferably in the range between 10 and 30 $Kg/cm^2$-G. Temperatures at the top and the bottom of the distillation apparatus are determined depending on the operation pressure and compositions of the distillate product and the bottom product. In order to carry out the distillation operation economically considering operation temperatures of a condenser and a reboiler, the temperature at the top of the distillation apparatus is preferably in the range from −48 to 50° C., and the temperature at the bottom of the distillation apparatus is preferably in the range from −20 and 150° C.

The process of the present invention may be carried out in a batch mode or a continuous mode. Although in some cases, the process may be carried out in a semi-continuous mode wherein withdrawal and/or feed is carried out intermittently, the extractant should be continuously supplied to the distillation apparatus.

In the process of the present invention, a ratio (S/F) of an amount (S) of the extractant to an amount (F) of the feed mixture (namely, HFC-125 and CFC-115) has an effect on an extent of the separation. Generally, the ratio may be properly selected depending on a composition of HFC-125/CFC-115 of the mixture to be subjected to the extractive distillation, an allowable concentration of CFC-115 which remains in the separated HFC-125 and so on. A required number of theoretical plate of the extractive distillation apparatus may be properly selected in combination with the selection of the ratio (S/F).

In general, when the process of the present invention is carried out in a continuous mode, preferable separation may be achieved with the ratio based on weight in the range from about 1/5 to about 10/1, and preferably in the range from about 1 to about 3. For example, the following example can be shown: A mixture of CFC-115 (1 mol %) and HFC-125 (99 mol %) is subjected to the extractive distillation using the extractant of any of the ethyleneglycol-based compounds, whereby CFC-115 is distilled in a concentration increased up to 10 mol % (thus, 90 mol % of HFC-125) and also an HFC-125 stream is finally obtained of which CFC-115 concentration is not more than 0.1 mol % (thus, more than 99.9 mol % of HFC-125) after the separation from the extractant. In order to achieve this separation, it is sufficient that the required number of theoretical plate in the extractive distillation is in the range of for example about 10 to 30 and the weight ratio of the extractant to the mixture consisting of HFC-125 and CFC-115 is in the range of for example about 1 to 3.

The present invention will be explained in detail with reference to FIG. 1 by way of an example in which diethyleneglycol di-tert-butylether is used as the extractant inclusive re-use thereof.

A mixture 2 comprising HFC-125 and CFC-115 (for example HFC-125/CFC-115=99 mol %/1 mol %) is supplied to an extractive distillation apparatus 1 which is operated under a pressurized condition (for example 10 $Kg/cm^2$-G).

For example, an apparatus having the number of theoretical plate of about twenty is used as the distillation apparatus 1. Extractant 3 is supplied to the distillation apparatus 1 (for example, onto the third theoretical plate from the top) in an amount of about 1.5 times by weight of that of the mixture 2. Under those conditions, for example, when the mixture is supplied onto the tenth theoretical plate from the top and a reflux ratio is set for one hundred, a mixture of HFC-125/CFC-115 (for example 90 mol %/10 mol %) may be withdrawn from the top as a distillate product 4.

In addition, a mixture containing extractant and HFC-125/CFC-115 (for example 99.9 mol %/0.1 mol %) may be withdrawn from the bottom as a bottom product 5 (extractant concentration is 60% by weight). Then, the bottom product may be supplied to a distillation apparatus 9 which is operated under a pressurized condition (for example 25 $Kg/cm^2$-G), and HFC-125 substantially free of CFC-115 and extractant may be obtained as a distillate product 6 from the top. Extractant which is substantially free of HFC-125 is recovered from the bottom of the distillation apparatus 9 as a bottom product 7, which is then supplied to the extractive distillation apparatus 1 to re-use as the extractant. The extractant to be re-used may be optionally heated or cooled as required through a heat exchanger 8 before being supplied to the distillation apparatus 1.

In the process of the present invention, the level of the plate onto which the extractant is supplied is preferably above a plate onto which the mixture is supplied in any of the extractants is used. Thus, the plate onto which a reflux is returned and the plate onto which the extractant is supplied may be the same. Optionally, the plate onto which the mixture is fed and the plate onto which the extractant is supplied may be the same. Alternatively, before the mixture is fed to the distillation apparatus, it may be mixed with the extractant and then the resulted mixture may be supplied to the distillation apparatus.

Concretely, when diethyleneglycol is used as the extractant, it is more preferable to supply diethyleneglycol onto a plate which is located about 3 to 5 theoretical plates above a plate onto which the mixture is supplied.

Employing the apparatus and the operation conditions as described above, HFC-125 which is free of CFC-115 can be separated from the mixture comprising HFC-125 and CFC-115.

EXAMPLE

Using an extractive distillation column equipped with a condenser at its top, a mixture of HFC-125 and CFC-115 (=99/1 (wt/wt)) was treated. The distillation column had a diameter of 100 mm and 10 theoretical plates (actual plate number was 15), and it was operated under a pressure of about 10 $Kg/cm^2$-G. Diethyleneglycol monometylether as the extractant was supplied onto the third theoretical plate from the top, and the mixture to be distilled was supplied at a temperature of 50° C. onto the fifth theoretical plate from the top.

Concentrated CFC-115 which contains HFC-125 was withdrawn as a distillate product from the top. This operation was carried out at a reflux ratio of 200. A mixture of HFC-125 and diethyleneglycol monometylether was withdrawn from the bottom at a temperature of 50° C., which is free of CFC-115.

Mass balance of the above operation is shown in Table 2 below:

TABLE 2

| | total flow rate (Kg/hr) | HFC-125 (wt %) | CFC-115 (wt %) | CH$_3$O(CH$_2$CH$_2$O)$_2$H (wt %) |
|---|---|---|---|---|
| (input) | | | | |
| Extractant | 60 | | | 100 |
| HFC-125/ CFC-115 mixture | 40 | 99 | 1 | |
| (output) | | | | |
| Distillate product | 0.4 | 96 | 4 | 0.1 |
| Bottom product | 99 | 39.99 | 0.01 | 60 |

The bottom product withdrawn from the bottom of the distillation apparatus, which contained HFC-125, methanol and small amount of CFC-115 was supplied to another distillation apparatus having a diameter of 80 mm and 5 theoretical plates (the number of actual plate was 7) which was operated under an operation pressure of 18 Kg/cm$^2$-G and a reflux ratio of 10, whereby a distillate product having a ratio of HFC-125 (99.99 weight %)/CFC-115 (0.01 weight %) was obtained from the top and diethyleneglycol monometylether stream containing 3% by weight of HFC-125 was obtained from the bottom as a bottom product. Thus obtained diethyleneglycol monometylether stream can be re-used as the extractant for the extractive distillation.

What is claimed is:

1. A process of producing pentafluoroethane by subjecting a mixture comprising at least pentafluoroethane and chloropentafluoroethane to an extractive distillation step to obtain pentafluoroethane which is substantially free of chloropentafluoroethane, which process is characterized by supplying the mixture to the extractive distillation step, supplying, as an extractant to the extractive distillation step, at least one compound selected from ethyleneglycol-based compounds (excluding ethyleneglycol and diethyleneglycol) having a general formula:

wherein R$^1$ and R$^2$ may be the same or different and are each independently selected from the group consisting of hydrogen and an alkyl group having 1 to 4 carbon atoms, and n is an integer with a value from 1 to 3; and obtaining a mixture comprising pentafluoroethane and the extractant as the main component thereof as a bottom product from the extractive distillation step.

2. The process according to claim 1 wherein the mixture and the extractant are mixed together, which is then supplied to the extractive distillation step.

3. The process according to claim 1 wherein a weight ratio (S/F) of the extractant (S) used in the extractive distillation step to pentafluoroethane and chloropentafluoroethane (F) which are contained in the mixture to be supplied to the extractive distillation step is in the range from 0.2 to 10.

4. The process according to claim 1 wherein pentafluoroethane is separated by distilling the mixture comprising pentafluoroethane and the extractant as the main component thereof as a bottom product from the extractive distillation step, whereby a mixture containing the extractant as a main component thereof is recovered and re-used in the extractive distillation step.

5. The process according to claim 1 wherein the extractant is ethyleneglycol mono-alkylether or polyethyleneglycol mono-alkylether.

6. The process according to claim 1 wherein the extractant is ethyleneglycol dialkylether or polyethyleneglycol dialkylether.

7. The process according to claim 1 wherein the extractant is triethyleneglycol.

* * * * *